(12) United States Patent
Freedman

(10) Patent No.: US 6,736,141 B2
(45) Date of Patent: May 18, 2004

(54) SURGICAL AID

(76) Inventor: David L. Freedman, 45 McCrea Street, Swan Hill, Victoria 3585 (AU)

( * ) Notice: Subject to any disclaimer, the term of this patent is extended or adjusted under 35 U.S.C. 154(b) by 213 days.

(21) Appl. No.: 09/737,907

(22) Filed: Dec. 15, 2000

(65) Prior Publication Data

US 2002/0077635 A1 Jun. 20, 2002

(51) Int. Cl.[7] .............................................. A61B 17/00
(52) U.S. Cl. ...................... 128/850; 128/887; 128/888; 606/148
(58) Field of Search ................................ 606/151, 148, 606/153, 157, 213, 215, 232; 128/850, 851, 887, 888

(56) References Cited

U.S. PATENT DOCUMENTS

| | | | | | |
|---|---|---|---|---|---|
| 1,618,261 | A | * | 2/1927 | Arbogast | 600/210 |
| 3,342,183 | A | * | 9/1967 | Edenbaum | 424/448 |
| 4,370,981 | A | * | 2/1983 | Sanderson | 606/215 |
| 4,964,417 | A | * | 10/1990 | Peters | 128/850 |
| 6,383,201 | B1 | * | 5/2002 | Dong | 606/151 |
| 6,395,015 | B1 | * | 5/2002 | Borst et al. | 606/153 |

FOREIGN PATENT DOCUMENTS

| AT | 139806 | 2/2000 |
|---|---|---|

OTHER PUBLICATIONS

Glassman Viscera Retainer, "Th Fish", Nov. 1999, ADEPT-MED International.*

* cited by examiner

Primary Examiner—Danny Worrell
(74) Attorney, Agent, or Firm—Baker & Daniels

(57) ABSTRACT

A surgical aid to facilitate wound closure particularly, but not exclusively, in the abdominal region. The surgical aid includes a body portion and a tail portion. At least the body portion is made predominantly of a planar, flexible and resiliently stretchable material, preferably surgical grade silicone. In a preferred embodiment the surgical aid is fish shaped, having a roughly elliptical body and a smaller elliptical tail. The body and tail portions are integrally formed from a single sheet of surgical grade silicone. The invention also provides a method of using the surgical aid wherein the body portion is inserted into the wound prior to closure to act as a physical barrier between the peritoneum and the viscera. The peritoneum and posterior rectus sheath is then closed by suturing over the body portion. When the closure is almost complete, the body portion is withdrawn using the tail portion as a handle. The closure can then be completed. The surgical aid serves to make wound closure faster, easier and safer by reducing the risk of needle stick injury to the operating staff and needle perforation injury to the patient.

18 Claims, 3 Drawing Sheets

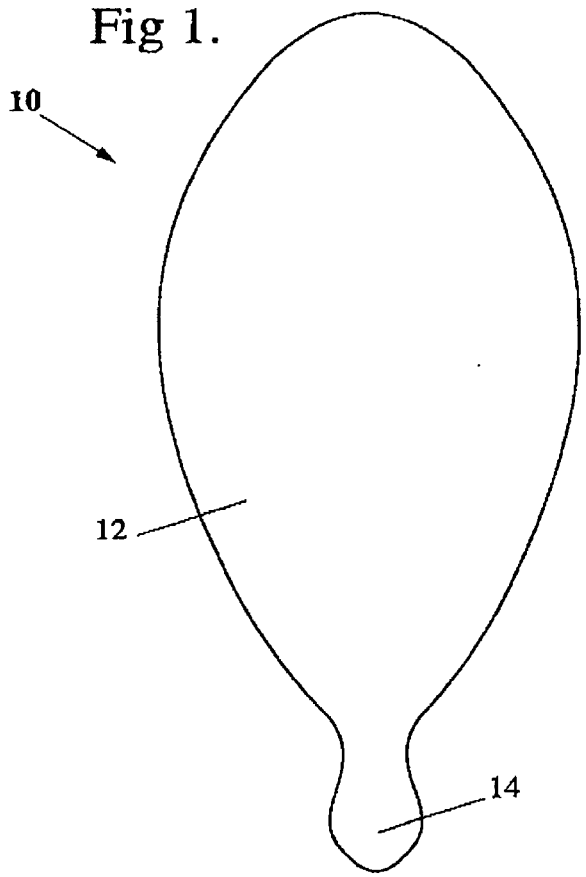
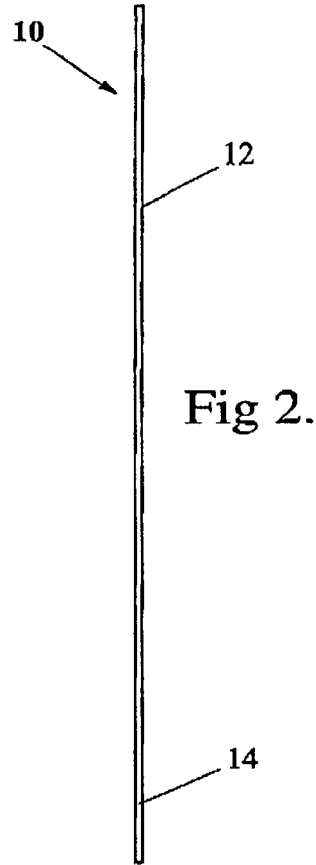
Fig 1.
Fig 2.
Fig 3.
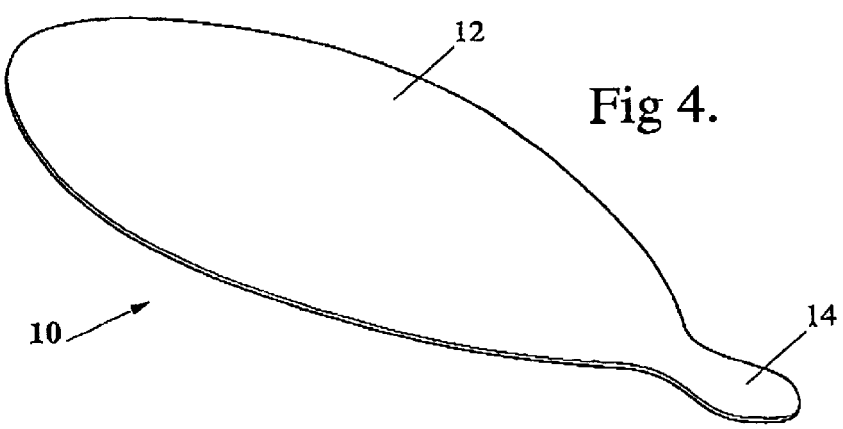
Fig 4.

SURGICAL AID

FIELD OF THE INVENTION

The present invention relates generally to surgical devices. In particular, the invention concerns a surgical aid to facilitate closure of a wound following a surgical procedure. The surgical aid is especially useful in abdominal surgery and it will be convenient to hereinafter describe the invention in relation to that example application. It should be understood however that the surgical aid is not limited to abdominal surgery and is capable of wider application and use.

BACKGROUND

Following surgery in the abdominal region, a wound, often of considerable size, needs to be closed by suturing. This is a delicate and time-consuming procedure as the surgeon must carefully suture the various membranes of the abdomen back together whilst being very cautious not to nick or puncture the soft internal organs of the abdomen, known as the viscera.

The procedure is made even more difficult if the patient is overweight because there is a greater need to retain, or hold down, the viscera whilst simultaneously pulling together the edges of the membrane being sutured, such as the peritoneum and posterior rectus sheath. In this situation, the risk of nicks or punctures to internal organs such as the bowel becomes even greater.

To alleviate this problem, surgeons have occasionally used a rectangular piece of rubber, or similar, to retain the viscera and provide a physical barrier against accidental nicks or punctures. The rubber was inserted into the wound over the viscera prior to closure. The wound was then partially closed, by suturing together the edges of the peritoneum, over the rubber, until a hole of sufficient size to remove the rubber remained. The rubber was then removed through that hole and the remainder of the wound closed. This procedure did to some extent address the problem but the stiffness of rubber and the awkward shape made it difficult to remove the piece of rubber from the wound.

One known device, sold under the name Glassman Viscera Retainer, the "Fish" by Adept-Med International Inc. partly addresses this problem. It includes a viscera retaining part, to be inserted into the wound, and a circular ring, to act as a handle to facilitate extraction of the retaining part from the wound. The retaining part includes a roughly diamond shaped, pliable web extending from a solid central rib. Attached to an end of the rib is a string, and at the end of the string is the circular ring. In use, the retaining part is inserted into the wound prior to closure and the wound is then partially closed by suturing over it. The retaining part is then withdrawn by pulling on the string using the ring. It has been found, however, that the solid central rib reduces the ability to remove the retaining part through a small hole. Also, the device is made of a material that cannot be sterilised and re-used. It must be discarded after a single use.

There therefore remains a need for a surgical aid of this type which is easier to use, can be withdrawn through a smaller hole upon partial closure of the wound and which can be re-used in subsequent surgical procedures.

SUMMARY OF THE INVENTION

The present invention provides a surgical aid to facilitate wound closure. The surgical aid includes a body portion and a tail portion. At least the body portion is made predominantly of a planar, flexible and resiliently stretchable material.

The surgical aid is especially useful to facilitate closing of a wound following abdominal surgery. In use, the body portion is inserted into the wound prior to closure, to act as a physical barrier protecting the viscera. The tail portion is not inserted into the wound and remains accessible to facilitate later withdrawal of the body portion from the wound. The peritoneum, posterior rectus sheath or other membrane/layer being closed, is then drawn together and sutured over the body portion of the surgical aid until only a small hole is left, with the tail portion still being accessible outside the wound. The body portion is then withdrawn from the wound by pulling on the tail portion.

The invention is based on a realisation that, in this application, a resiliently stretchable material exhibits special properties which become extremely useful. If tension is applied to a planar piece of such a material, it will have a natural tendency to curl or fold in a direction lateral to the direction of the tension. Thus, in this application, when tension is applied to the body portion of the surgical aid by pulling on the tail portion, the body portion tends to curl, or at least fold. This makes it much easier to pull the body portion of the surgical aid through an opening which is smaller than with prior art devices. In turn, this further reduces the risk of nicks or punctures to the delicate tissue and organs of the viscera whilst the surgeon is closing the remaining section of the wound.

According to the invention, the material must be flexible and, at least to some extent, resiliently stretchable. The degree of stretchability is not critical. It merely needs to be sufficient to encourage a rolling or folding action of the body portion when tension is applied.

In one embodiment, at least the body portion is made solely of a planar, flexible and resiliently stretchable material. Preferably, the body portion is made of surgical grade silicone. More preferably, the body portion includes a silicone rubber compound sold under the name SILASTIC® K760 by Dow Corning. In this application, this material makes it possible to withdraw the surgical aid through an even smaller opening. When in contact with body fluids present during surgery, the surface of the material slides easily with respect to the body tissue of the patient. This further facilitates withdrawal of the surgical aid from the wound.

Surgical grade silicone can also be sterilised in an autoclave, thus making it possible to re-use the surgical aid many times. It does not need to be disposed of after a single use, thereby reducing medical waste.

In a preferred embodiment, at least the body portion is impregnated with barium sulphate to render it radiopaque. In this way, if by any chance, a fragment of the surgical aid remained within the abdomen of the patient after the wound had been closed, it would be detectable in an x-ray.

In a preferred embodiment, the body and tail portions of the surgical aid are integrally formed from a single sheet of material. This reduces manufacturing costs and means that there is no joint in the region between the body and tail portions. This region is merely a narrowed section of the same material which can fold or roll as required to be drawn through a small opening in the wound. The material is preferably of a thickness between 1 and 3 mm, and more preferably between 1.5 and 2.0 mm.

The body portion of the surgical aid is preferably elliptical in shape and, in the preferred embodiment, has a length to width ratio of about 2:1. This ratio has been found to be suitable for a wide range of surgical procedures.

The optimum size of the surgical aid will depend on the size of the wound being closed and the size of the patient. The width of the body portion of the surgical aid is preferably between 100 and 200 mm, and more preferably between 130 and 160 mm. The length of the body portion is preferably between 150 and 400 mm, and more preferably between 200 and 300 mm.

The surgical aid may conveniently be formed in the shape of a fish having a relatively large body portion and a relatively small tail portion. In one form, both the body portion and the tail portion are roughly elliptical in shape, with the region connecting the two portions forming a narrow waist.

The preferred form of the surgical aid, being made from a single sheet of surgical grade silicone, has a further advantage over the prior art device by Adept-Med in that it is far cheaper to manufacture. The prior art surgical device includes multiple parts, such as the solid rib and the pliable membrane, which need to be moulded to form the complete device. Also, a separate string and ring handle need to be attached. In contrast, the surgical aid of the present invention can be merely stamped out of a continuous sheet of the chosen material, such as surgical grade silicone.

Another aspect of the present invention provides a method of closing a wound following a surgical procedure. The method includes providing a surgical aid of the type described above and inserting the body portion of the surgical aid into the wound to act as a physical barrier between underlying tissue and a membrane to be closed. The tail portion is left outside the wound and remains accessible. The membrane is then partially closed by suturing over the body portion and when the wound is almost closed, the body portion is withdrawn by pulling on the tail portion. Closure of the wound is then completed.

A further aspect of the present invention provides a method of closing a wound following abdominal surgery. The method includes providing a surgical aid of the type described above and inserting the body portion of the surgical aid into the wound to act as a physical barrier between the peritoneum and the viscera. The tail portion is left outside the wound and remains accessible. The peritoneum and posterior rectus sheath are then partially closed by suturing over the body portion and when the wound is almost closed, the body portion is withdrawn by pulling on the tail portion. Closure of the wound is then completed.

A still further aspect of the present invention is the use of a surgical aid of the type described above to facilitate wound closure.

It will be convenient to hereinafter describe the invention by reference to the accompanying drawings which illustrate a preferred embodiment thereof. Other embodiments of the invention are possible, and consequently the particularity of the accompanying drawings is not to be understood as superceding the generality of the preceding description of the invention.

BRIEF DESCRIPTION OF THE DRAWINGS

In the drawings;

FIG. 1 illustrates a top plan view of a surgical aid made in accordance with a preferred embodiment of the invention;

FIGS. 2 and 3 illustrate side and end views, respectively, of the surgical aid shown in FIG. 1;

FIG. 4 illustrates a perspective view of the surgical aid shown in FIG. 1;

DETAILED DESCRIPTION OF A PREFERRED EMBODIMENT

Referring firstly to FIGS. 1 to 4, there is shown a surgical aid 10 in accordance with a preferred embodiment of the invention, for facilitating wound closure following surgery in the abdominal region of a patient. The surgical aid 10 is approximately fish shaped, having a relatively large body portion 12 and a relatively small tail portion 14, and is formed from a single piece of surgical grade silicone rubber. A narrow waist is formed between body portion 12 and tail portion 14. In the embodiment shown in FIG. 1, body portion 12 has a longitudinal dimension of about six times the longitudinal dimension of tail portion 14. Additionally, body portion 12 has a lateral dimension about 6.7 times the lateral dimension of the narrow waist. This material is flexible and resiliently stretchable.

In one embodiment the material includes a silicone rubber compound sold tinder the name SILASTIC® K760 by Dow Corning. This compound is a 60 durometer general purpose silicone rubber compound designed for use in a variety of moulded parts. It can be blended with other SILASTIC® brand silicone rubbers to obtain intermediate hardness.

The components of SILASTIC® K760 silicone rubber are listed in 21 CFR 177.2600. This FDA (Federal Drug Administration) regulation deals with rubber articles intended for repeated use in contact with food. 21 CFR 177.2600 is incorporated herein by cross-reference.

The properties of SILASTIC® K760 are outlined in Dow Corning's product information sheet "SILASTIC® K760 Silicone Rubber". This product information sheet is incorporated herein by cross-reference.

Whilst SILASTIC® K760 silicone rubber is the predominant compound used in the material of the present embodiment of the surgical aid, other compounds may also be included to vary the desired properties. Also, any other silicone rubber material approved by the FDA for surgical use, or any other approved material having the necessary flexibility and stretchability, may alternatively be used.

To ensure that fragments of the surgical aid are not left undetected within the abdomen of the patient after the wound has been closed, the silicone material is impregnated with barium sulphate to render it radiopaque. In this way, if a fragment were left within the body, it would be detectable using a conventional xray.

Figure 5:
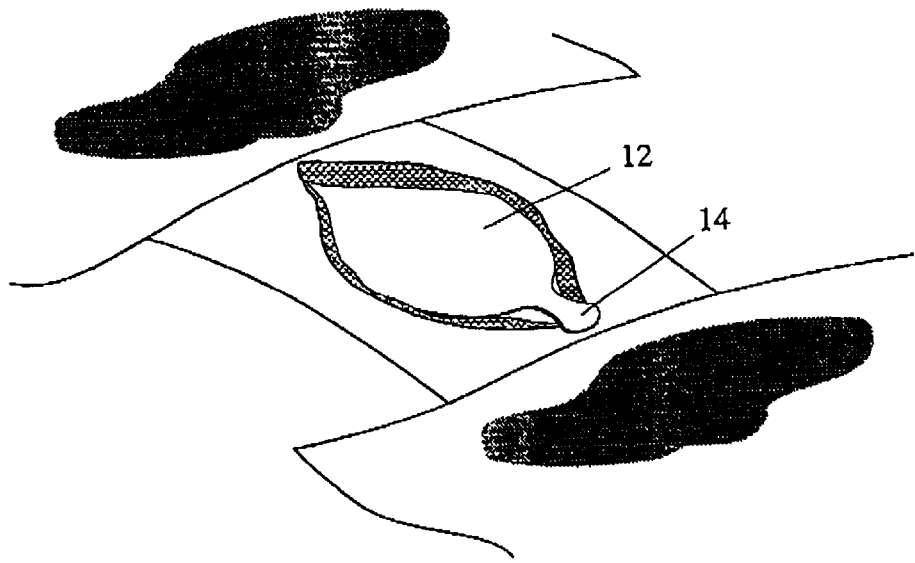
FIG. 5 illustrates the surgical aid of FIG. 1 in use wherein the aid has been inserted into a wound prior to closure.

FIGS. 5 to 8 show the surgical aid in use. As shown in FIG. 5, the body portion 12 of the surgical aid 10 is introduced into the abdominal wound before closure. It acts as a physical barrier between the peritoneum and the viscera. The tail portion 14 of the surgical aid 10 remains accessible outside the wound.

Figure 6:
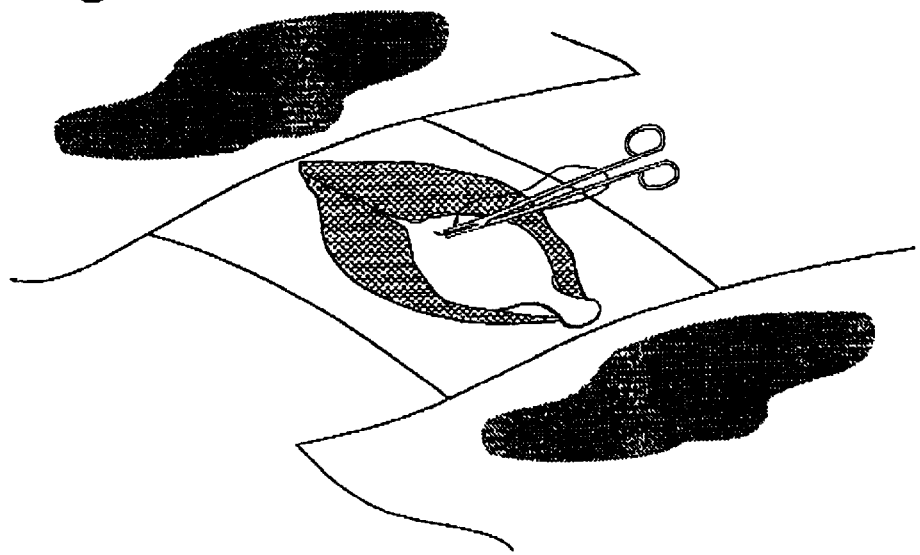
FIGS. 6 and 7 illustrate the wound partially closed.
Figure 7:
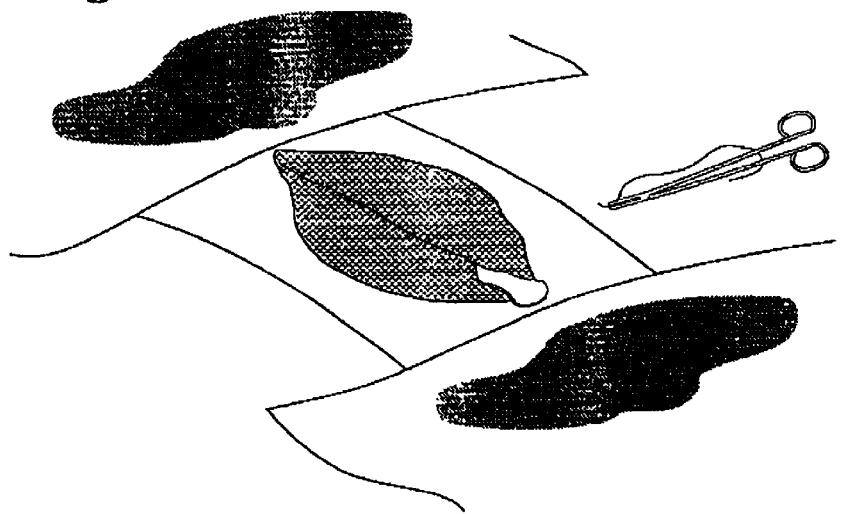
Figure 8:
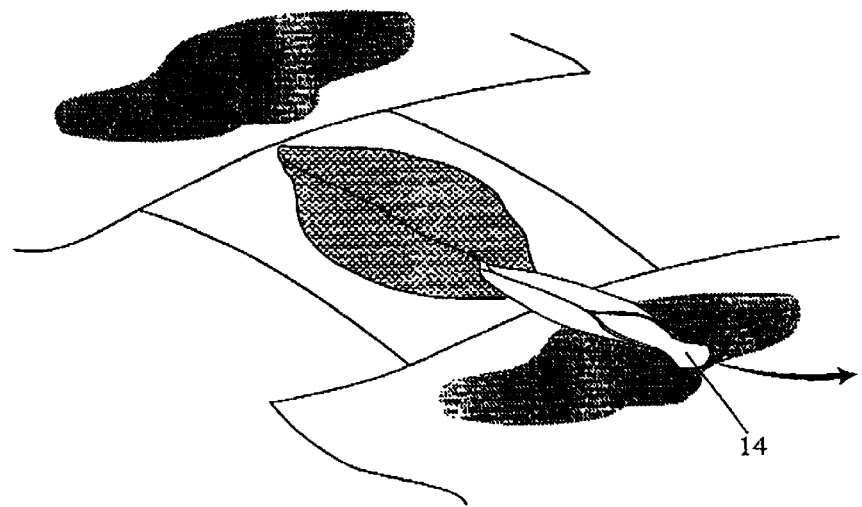
FIG. 8 illustrates withdrawal of the surgical aid through a small opening remaining in the wound.

The peritoneum and posterior rectus sheath is partially closed by suturing over the body portion 12 of the surgical aid 10 (FIG. 6). When the closure is almost compete (FIG. 7), the body portion 12 is withdrawn from the wound by pulling on the tail portion 14 (FIG. 8). The anterior rectus sheath is then sutured to complete closure of the fibroaponeurotic layers.

The surgical aid of the present invention thus makes wound closure faster and easier, and reduces the risk of needle stick and needle perforation injury, to both the viscera of the patient and to the surgeon.

It has been found that the surgical aid of the invention may be manufactured in two sizes to cater for almost all situations. A standard size, being 300×130×1.5 mm is suitable in most instances. This size can be removed through a hole little more than one finger's breadth in diameter. A large size, being 350×156×2.0 mm, has been designed for use in long mid-line incisions.

Although a preferred embodiment of the invention has been described herein in detail, it will be understood by those skilled in the art that variations may be made thereto without departing from the spirit of the invention or the scope of the appended claims. For example, the tail portion of the surgical aid may be made of any desired shape, such as for example a true fish tail shape, or it may be enlarged and include a hole to enable a surgeon to place a finger within the hole to more easily withdraw the body portion from the wound. Such variations to the disclosed surgical aid are considered to fall within the scope of the appended claims.

I claim:

1. A surgical aid to facilitate wound closure including a body portion and a tail portion integrally formed from a single sheet of planar, flexible and resiliently stretchable material, both the body portion and the tail portion being substantially elliptical in shape with a region connecting the portions forming a narrow waist, the body portion having a longitudinal dimension about six times the longitudinal dimension of the tail portion and having a lateral dimension about 6.7 times greater than the lateral dimension of the narrow waist.

2. A surgical aid as defined in claim 1 wherein at least the body portion is made of surgical grade silicone.

3. A surgical aid as defined in claim 1 wherein at least the body portion is impregnated with barium sulphate to render it radiopaque.

4. A surgical aid as defined in claim 1 wherein the degree of stretchability of the material is sufficient to cause at least the body portion to curl or fold when a tension is applied thereto by pulling on the tail portion.

5. A surgical aid as defined in claim 1 wherein the material is between 1 and 3 mm thick.

6. A surgical aid as defined in claim 1 wherein the material is between 1.5 and 2.0 mm thick.

7. A surgical aid as defined in claim 1 wherein the body portion is substantially elliptical in shape and has a length to width ratio of about 2:1.

8. A surgical aid as defined in claim 7 wherein the width of the body portion is between 100 and 200 mm.

9. A surgical aid as defined in claim 7 wherein the width of the body portion is between 130 and 160 mm.

10. A surgical aid as defined in claim 7 wherein the length of the body portion is between 115 and 400 mm.

11. A surgical aid as defined in claim 7 wherein the length of the body portion is between 200 and 300 mm.

12. A surgical aid as defined in claim 1 wherein the surgical aid is formed in the shape of a fish having a relatively large body portion and a relatively small tail portion.

13. A surgical aid as defined in claim 1 wherein at least the body portion is made solely of a planar, flexible and resiliently stretchable material.

14. A method of closing a wound following a surgical procedure, the method including the steps of:

providing a surgical aid, the surgical aid including a body portion and a tail portion integrally formed from a single sheet of planar, flexible and resiliently stretchable material, both the body portion and the tail portion being substantially elliptical in shape with a region connecting the portions forming a narrow waist, the body portion having a longitudinal dimension about six times the longitudinal dimension of the tail portion and having a lateral dimension about 6.7 times greater than the lateral dimension of the narrow waist;

inserting the body portion into the wound to act as a physical barrier between underlying tissue and a membrane to be closed, the tail portion remaining accessible outside the wound;

partially closing the membrane by suturing over the body portion;

when the closure is almost complete, withdrawing the surgical aid by pulling on the exposed tail portion; and completing the closure of the membrane.

15. A method of closing a wound as defined in claim 14 wherein at least the body portion of the surgical aid is made of surgical grade silicon.

16. A method of closing a wound as defined in claim 14 wherein the body portion and the tail portion of the surgical aid are integrally formed from a single sheet of material.

17. A method of closing a wound as defined in claim 14 wherein the surgical aid is formed in the shape of a fish having a relatively large body portion and a relatively small tall portion.

18. A method of closing a wound following abdominal surgery, the method including the steps of:

providing a surgical aid, the surgical aid being made of a single sheet of planar, flexible and resiliently stretchable material and being in the shape of a fish having an integrally formed body portion and a tail portion, both the body portion and the tail portion being substantially elliptical in shape with a region connecting the portions forming a narrow waist, the body portion having a longitudinal dimension about six times the longitudinal dimension of the tail portion and having a lateral dimension about 6.7 times greater than the lateral dimension of the narrow waist;

inserting the body portion of the surgical aid into the wound to act as a physical barrier between the peritoneum and the viscera, the tail portion remaining accessible outside the wound;

partially closing the peritoneum by suturing over the body portion;

when the closure is almost complete, withdrawing the surgical aid by pulling on the exposed tail portion; and completing the closure of the peritoneum and then the subsequent membranes.

* * * * *

UNITED STATES PATENT AND TRADEMARK OFFICE
CERTIFICATE OF CORRECTION

PATENT NO. : 6,736,141 B2  Page 1 of 1
DATED : May 18, 2004
INVENTOR(S) : David L. Freedman It is certified that error appears in the above-identified patent and that said Letters Patent is hereby corrected as shown below:

Column 6,
Line 35, delete "tall" and substitute therefor -- tail --

Signed and Sealed this

Thirteenth Day of July, 2004

JON W. DUDAS
*Acting Director of the United States Patent and Trademark Office*